US012653802B2

(12) United States Patent
Tsai et al.

(10) Patent No.: US 12,653,802 B2
(45) Date of Patent: Jun. 16, 2026

(54) METHOD FOR TREATING LUNG CANCER

(71) Applicant: Mien-chie Hung, Taichung City (TW)

(72) Inventors: Chang-hai Tsai, Taichung City (TW); Mien-chie Hung, Taichung City (TW); Sheng-chu Kuo, Tainan City (TW); Pei-chih Lee, Taichung City (TW); Min-tsang Hsieh, Taichung City (TW); Shin-hun Juang, Taipei City (TW); Hui-yi Lin, Taichung City (TW)

(73) Assignee: Mien-chie Hung, Taichung City (TW)

( * ) Notice: Subject to any disclaimer, the term of this patent is extended or adjusted under 35 U.S.C. 154(b) by 334 days.

(21) Appl. No.: 18/267,691

(22) PCT Filed: Dec. 14, 2021

(86) PCT No.: PCT/CN2021/137647

§ 371 (c)(1),
(2) Date: Jun. 15, 2023

(87) PCT Pub. No.: WO2022/127751

PCT Pub. Date: Jun. 23, 2022

(65) Prior Publication Data

US 2024/0000742 A1 Jan. 4, 2024

Related U.S. Application Data

(60) Provisional application No. 63/126,849, filed on Dec. 17, 2020.

(51) Int. Cl.

*A61K 31/216* (2006.01)
*A61K 31/506* (2006.01)
*A61K 31/5377* (2006.01)
*A61P 35/00* (2006.01)

(52) U.S. Cl.

CPC .......... *A61K 31/216* (2013.01); *A61K 31/506* (2013.01); *A61K 31/5377* (2013.01); *A61P 35/00* (2018.01)

(58) Field of Classification Search

CPC ................ A61K 31/216; A61K 31/506; A61K 31/5377; A61P 35/00

See application file for complete search history.

(56) References Cited

U.S. PATENT DOCUMENTS

2005/0215635 A1 9/2005 Rafi et al.

FOREIGN PATENT DOCUMENTS

| | | | |
|---|---|---|---|
| CN | 105476996 A | 4/2016 | |
| CN | 109689608 A | 4/2019 | |
| JP | 2008516954 A | 5/2008 | |
| TW | I405566 B | 8/2013 | |
| TW | 201713323 A | 4/2017 | |
| TW | 201742855 A | 12/2017 | |
| WO | WO-2017218219 A1 * | 12/2017 | ........... C07C 49/255 |

OTHER PUBLICATIONS

Lee, J.-Y. et al. Curcumin Induces EGFR Degradation in Lung Adenocarcinoma and Modulates p38 Activation in Intestine: The Versatile Adjuvant for Gefitinib Therapy. PLoS One 2011, 6, e23756. (Year: 2011).*

Bimonte, S. et al. Dissecting the Role of Curcumin in Tumour Growth and Angiogenesis in Mouse Model of Human Breast Cancer. BioMed Research International 2015, 1, 878134. (Year: 2015).*

Manolova, Y. et al. The effect of the water on the curcumin tautomerism: A quantitative approach. Spectrochimica Acta Part A: Molecular and Biomolecular Spectroscopy 2014, 132, 815-820. (Year: 2014).*

Yanagisawa, D. et al. Relationship between the tautomeric structures of curcumin derivatives and their Ab-binding activities in the context of therapies for Alzheimer's disease. Biomaterials 2010, 31, 4179-4185. (Year: 2010).*

Cancer treatment; Mayo Clinic. https://www.mayoclinic.org/tests-procedures/cancer-treatment/about/pac-20393344 (Accessed Sep. 22, 2025; Published Mar. 13, 2020) (Year: 2020).*

Hsieh, M.-T. et al. New bis(hydroxymethyl) alkanoate curcuminoid derivatives exhibit activity against triple-negative breast cancer in vitro and in vivo. European Journal of Medicinal Chemistry 2017, 131, 141-151. (Year: 2017).*

Caruso, Francesco , et al., "The in vitro antitumor activity of arene-ruthenium(II) curcuminoid complexes improves when decreasing curcumin polarity", Journal of Inorganic Biochemistry, published on Jun. 4, 2016, vol. 162, pp. 44-51, published by Elsevier Inc., United States.

Chen, Ping , et al., "Curcumin overcome primary gefitinib resistance in non-small-cell lung cancer cells through Inducing autophagy-related cell death", Journal of Experimental & Clinical Cancer Research, published on Jun. 13, 2019, vol. 38, Article No. 254, pp. 1-17, published by BioMed Central, United Kingdom.

(Continued)

*Primary Examiner* — Jeffrey H Murray
*Assistant Examiner* — Kristen W Romero

(57) ABSTRACT

A method for treating lung cancer is provided. The method includes administering a pharmaceutical composition including a diarylheptanoid compound or a pharmaceutically acceptable salt thereof to inhibit the growth of lung cancer cells. The diarylheptanoid compound has a structure shown in Formula (I), in which symbols in Formula (I) are as defined in the description.

Formula (I)

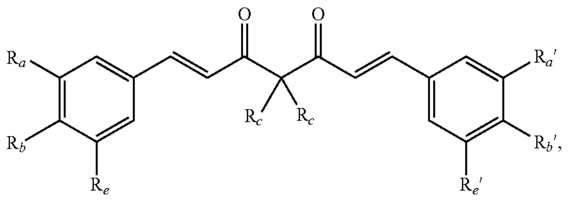

5 Claims, 7 Drawing Sheets

(56) References Cited

OTHER PUBLICATIONS

Das, R. P., et al., "Tuning the binding, release and cytotoxicity of hydrophobic drug by Bovine Serum Albumin hanoparticles: Influence of particle size", Colloids and Surfaces B: Biointerfaces, published on Jul. 24, 2017, vol. 158, pp. 682-688, published by Elsevier B.V., Netherlands.
Kumar, Anil , et al., "In Silico Inhibition Studies of Jun-Fos-DNA Complex Formation by Curcumin Derivatives", International Journal of Medicinal Chemistry, published on Dec. 6, 2012, vol. 2012, article ID 316972, pp. 1-8, published by Hindawi Publishing Corporation, Egypt.
Lozada-García, Maria Concepcion, et al., "Synthesis of Curcuminoids and Evaluation of Their Cytotoxic and Antioxidant Properties", Molecules, published on Apr. 14, 2017, vol. 22, issue 4, pp. 1-12, published by MDPI (Multidisciplinary Digital Publishing Institute), Switzerland.
Qiu, Xu , et al., "Synthesis and Identification of New 4-Arylidene Curcumin Analogues as Potential Anticancer Agents Targeting Nuclear Factor-kB Signaling Pathway", Journal of Medicinal Chemistry, published on Nov. 11, 2010, vol. 53, issue 23, pp. 8260-8273, published by American Chemical Society, United States.
Shaik, Noor Ahmad, et al., "Molecular designing, virtual screening and docking study of novel curcumin analogue as mutation (S769L and K846R) selective inhibitor for EGFR", Saudi Journal of Biological Sciences, published on May 25, 2018, vol. 26, issue 3, pp. 439-448, published by Elsevier B.V., Netherlands.
Li, Shanqun , et al., "Curcumin Lowers Erlotinib Resistance in Non-Small Cell Lung Carcinoma Cells With Mutated EGF Receptor", Oncology Research, published on Feb. 11, 2014, vol. 21, No. 3, pp. 137-144, published by Tech Science Press, United States.
Wada, Koji , et al., "Novel curcumin analogs to overcome EGFR-TKI lung adenocarcinoma drug resistance and reduce EGFR-TKI-induced GI adverse effects", Bioorganic & Medicinal Chemistry, author manuscript version, final edited form published on Feb. 13, 2015, vol. 23, issue 7, pp. 1507-1514, published by Elsevier, United States.
Xin, Jin , et al., "Curcumin co-treatment ameliorates resistance to gefitinib in drug-resistant NCI-H1975 lung cancer cells", Journal of Traditional Chinese Medicine, published on Jun. 15, 2017, vol. 37 issue 3, pp. 355-360, published by China Association of Chinese Medicine and China Academy of Chinese Medical Sciences, China, P.R.C.
Ye, Ming-Xiang , et al., "Curcumin: Updated Molecular Mechanisms and Intervention Targets in Human Lung Cancer", International Journal of Molecular Sciences, published on Mar. 22, 2012, vol. 13, issue 3, pp. 3959-3978, published by MDPI (Multidisciplinary Digital Publishing Institute), Switzerland.
Faridah Abas et al., "Biological Evaluation of Curcumin and Related Diarylheptanoids", Zeitschrift fur Naturforschung C: A journal of Biosciences, published on Oct. 1, 2006, vol. 61, issue 9-10, pp. 625-631, published by Verlag der Zeitschrift fur Naturforschung, Germany.
Min-Tsang Hsieh et al., "New bis(hydroxymethyl) alkanoate curcuminoid derivatives exhibit activity against triple-negative breast cancer in vivo and in vitro", European Journal of Medicinal Chemistry, published on Mar. 8, 2017, vol. 131, pp. 141-151, published by Elsevier Masson SAS, France.
Lee, et al., "Curcumin Induces EGFR Degradation in Lung Adenocarcinoma and Modulates p38 Activation in Intestine: The Versatile Adjuvant for Gefitinib Therapy", PLOS One, published on Aug. 17, 2011, vol. 6, issue 8, pp. 1-15, published by the Public Library of Science (PLOS), United States.

* cited by examiner

METHOD FOR TREATING LUNG CANCER

RELATED APPLICATIONS

This application is a National Stage of International Application No. PCT/CN2021/137647, filed Dec. 14, 2021, which claims the benefits of priorities of U.S. Provisional Application No. 63/126,849, filed on Dec. 17, 2020, the content of which are incorporated herein by reference.

BACKGROUND

Technical Field

The present disclosure relates to a use of a pharmaceutical composition. More particularly, the present disclosure relates to a use of a pharmaceutical composition including a diarylheptanoid compound or a pharmaceutically acceptable salt thereof for treating lung cancer.

Description of Related Art

Cancer, also known as malignant tumor, is an abnormal proliferation of cells, and these proliferating cells may invade other parts of the body, which is a disease caused by abnormal control of cell division and proliferation mechanisms. There is an increasing trend in the number of people suffering from cancer worldwide, and about 20% of the cancer population in the world is lung cancer patients. The 5-year survival rate of lung cancer patients after treatment is still as low as about 15%, which has been the cancer with the highest death rate in the world for many years.

According to different biological characteristics, treatment and prognosis, lung cancer can be divided into small cell lung cancer and non-small cell lung cancer (NSCLC). About 85-90% of lung cancers are NSCLC, of which lung adenocarcinoma is the most common type of lung cancer in women and non-smoking patients. Treatment for lung cancer often depends on the age of patient, past medical history, current health status, type of cancer cells, and stage of the disease. Generally speaking, small cell lung cancer has the characteristics of rapid division and proliferation, and metastases may occur in a short period of time, so that systemic chemotherapy or radiation therapy is the main treatment. The growth of NSCLC is slower, and the occurrence of metastasis is also slower, so that the principle of treatment depends on the clinical stage of the disease. The radical treatment of early stage (stage I, II) NSCLC is still based on complete resection of the tumor by surgery. The treatment principle is mainly chemical drug therapy or chemical drug combined with radiation therapy for the locally extended stage (stage III) including patients with malignant pericardium or hydropleural effusion and distant metastases (stage IV) or patients whose physical condition cannot be surgically removed.

However, it is a thorny problem in the treatment of metastatic or advanced NSCLC that has undergone chemotherapy and relapsed. Current clinical studies have confirmed that epidermal growth factor receptor-tyrosine kinase inhibitors (EGFR-TKIs) can be used as the second-line treatment after the first-line chemotherapy fails. But about 40-80% of NSCLC patients have the EGFR gene mutation, which overexpresses the epidermal growth factor receptor, leading to rapid growth, metastasis and drug resistance of cancer. Almost all patients with the EGFR gene mutation relapse within two years after clinical treatment with EGFR-TKIs, and no effective drugs are available after relapse so far.

SUMMARY

According to one aspect of the present disclosure is to provide a method for treating a lung cancer including administering a pharmaceutical composition including a diarylheptanoid compound or a pharmaceutically acceptable salt thereof, wherein the diarylheptanoid compound has a structure represented by Formula (I):

Formula (I)

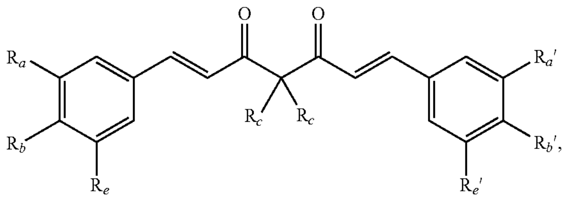

wherein $R_a$, $R_b$, $R_a'$ and $R_b'$ are independently H, C1-C2 alkyl, C1-C3 alkoxy, OH, or —OC(=O)$R_a$, wherein $R_d$ is C1-C3 alkyl or C1-C3 alkanol; $R_c$ is H, C1-C2 alkyl, C3-C6 unsaturated alkyl or C7-C12 arylalkyl with double or triple bonds; and $R_e$ and $R_e'$ are independently H, C1-C6 alkyl or C1-C6 alkoxy.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1A:
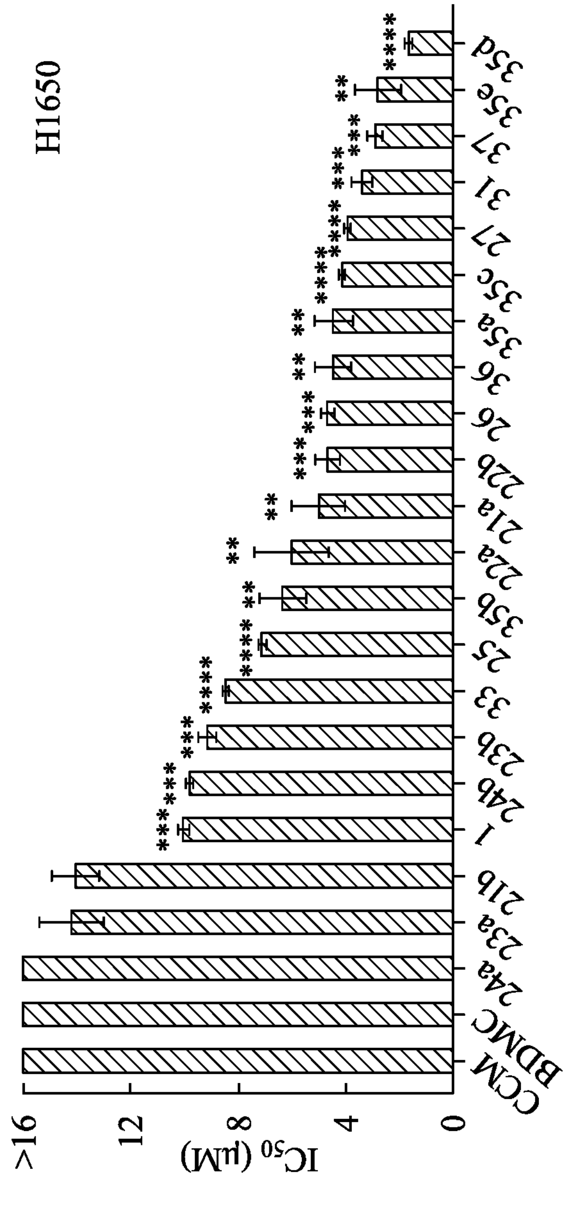
FIG. 1A shows the analysis result of the inhibition of H1650 cell growth by the diarylheptanoid compounds of the present disclosure.

The present disclosure provides a novel use of a pharmaceutical composition, and the pharmaceutical composition includes a diarylheptanoid compound or a pharmaceutically acceptable salt thereof, which can be used to manufacture a drug for treating a lung cancer. The diarylheptanoid compound of the present disclosure has a structure represented by Formula (I):

Formula (I)

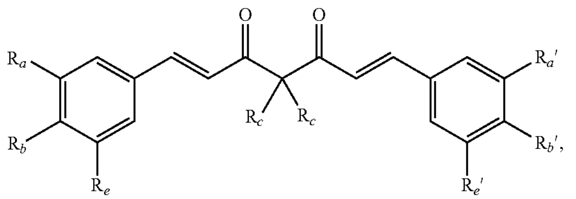

wherein $R_a$, $R_b$, $R_a$' and $R_b$' are independently H, C1-C2 alkyl, C1-C3 alkoxy, OH, or —OC(═O)$R_d$, wherein $R_d$ is C1-C3 alkyl or C1-C3 alkanol; $R_c$ is H, C1-C2 alkyl, C3-C6 unsaturated alkyl or C7-C12 arylalkyl with double or triple bonds; and $R_e$ and $R_e$' are independently H, C1-C6 alkyl or C1-C6 alkoxy.

At least one of $R_a$, $R_b$, $R_a$', and $R_b$' of the diarylheptanoid compound of the present disclosure can be —OC(═O)$R_d$, and $R_d$ is C1-C3 alkyl or C1-C3 alkanol. In addition, the diarylheptanoid compound can be interconvertible between keto and enol forms, when $R_c$ is H.

The pharmaceutical composition of the present disclosure can further include epidermal growth factor receptor-tyrosine kinase inhibitors (EGFR-TKIs), which can be combined with the diarylheptanoid compound or a pharmaceutically acceptable salt thereof. The EGFR-TKIs can be osimertinib, gefitinib, erlotinib or afatinib. The lung cancer treated by the pharmaceutical composition of the present disclosure can be non-small cell lung cancer (NSCLC). In addition, the lung cancer can be resistant to the EGFR-TKIs.

Unless otherwise noted, all terms, symbols or other scientific terms or terms used in the present disclosure have the meanings that are commonly understood by person having ordinary skill in the art. In some cases, terms with conventional meanings are defined herein for clarity and/or immediate reference, and the definitions incorporated herein should be construed as not necessarily substantial different from the conventional meanings in the art. Many of the techniques and procedures described or referenced herein are well known and routinely used by those skilled in the art. Where appropriate, unless otherwise stated, procedures for the use of commercially available kits and reagents are generally performed according to instructions and/or parameters defined by the manufacturer.

Unless contraindicated or noted otherwise, in these descriptions and throughout this specification, the terms "a" and "an" mean one or more (that is at least one). Furthermore, genera are recited as shorthand for a recitation of all members of the genus; for example, the recitation of C1-C3 alkyl is shorthand for a recitation of all C1-C3 alkyls including methyl, ethyl, propyl, and isomers thereof.

The diarylheptanoid compounds disclosed in the present disclosure and the pharmaceutically acceptable salt thereof can be verified by in vitro experiments, which can inhibit the growth of the EGFR-TKIs resistant NSCLC cells. It can further be verified by in vivo experiments that the compound disclosed in the specification and/or at least one pharmaceutically acceptable salt thereof can be administered to animals suffering from EGFR-TKIs resistant lung cancer (such as mouse model), and can obtain therapeutic effects. A positive result in one or more tests is sufficient to demonstrate the actual utility of the tested compound and/or salt, and an appropriate dosage range and administration route for animals (such as humans) can be determined based on test results.

Useful pharmaceutical dosage forms for administering the diarylheptanoid compound of the present disclosure and the pharmaceutically acceptable salt thereof include, but are not limited to, hard and soft gelatin capsules, tablets, parenteral injections and oral suspensions. The dosage administered can depend on factors including the age of the subject, the health and weight of the subject, the extent of the disease, the type of concomitant treatment (if any), the frequency of treatment and the nature of the desired effect. Usually the daily dose of active ingredient may vary, for example from 0.1 to 2000 mg per day. For example, 10-500 mg one or more times per day can be effective to achieve the desired results.

The same dosage form can generally be used when the diarylheptanoid compounds of the present disclosure and pharmaceutically acceptable salt thereof are administered stepwise or in combination with at least one other therapeutic agent. When drugs are administered in a physical combination, the dosage form and route of administration should be selected based on the compatibility of the combined drugs. Therefore, "co-administration" in the specification should be understood to include the concomitant or sequential administration of at least two agents, or as a fixed-dose combination of at least two active ingredients.

The diarylheptanoid compound and the pharmaceutically acceptable salt thereof in the specification can be used as the active ingredient alone, or administered in combination with at least one second active ingredient, the second active ingredient can be selected from, for example, other active ingredients known to be useful in the treatment of patients with NSCLC, in particular the EGFR-TKIs.

The following specific examples are used to further illustrate the present disclosure, in order to benefit the person having ordinary skill in the art, and can fully utilize and practice the present disclosure without excessive interpretation. These examples should not be regarded as limiting the scope of the present disclosure, but is used to illustrate how to implement the materials and methods of the present disclosure.

1. Structure of the Diarylheptanoid Compound of the Present Disclosure

The diarylheptanoid compound of the present disclosure uses curcumin (CCM) as a guiding compound to design a curcuminoid diarylheptanoid compound, which has a structure represented by Formula (I):

Formula (I)

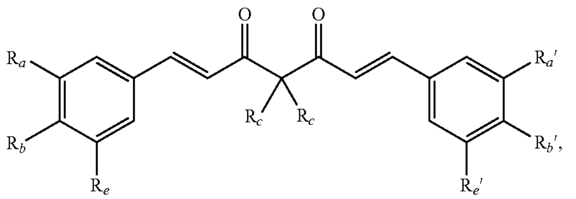

Please refer to the following Table 1, which shows $R_a$, $R_b$, $R_a$', $R_b$', $R_c$, $R_e$ is and $R_e$' of examples of the diarylheptanoid compound of the present disclosure—Compound 1, Compound 21a, Compound 21b, Compound 22a, Compound 22b, Compound 23a, Compound 23b, Compound 24a, Compound 24b, Compound 25, Compound 26, Compound 27, Compound 31, Compound 33, Compound 35a, Compound 35c, Compound 35d, Compound 35e, Compound 36 and Compound 37.

TABLE 1

| Compound | $R_a$ | $R_a'$ | $R_b$ | $R_b'$ | $R_c$ | $R_e$, $R_e'$ |
|---|---|---|---|---|---|---|
| 1 | OH | OH | $OCH_3$ | $OCH_3$ | H | H |
| 21a | $OCH_3$ | $OCH_3$ | 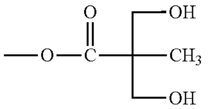 | 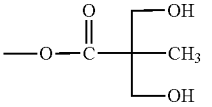 | H | H |
| 21b | $OCH_3$ | $OCH_3$ | 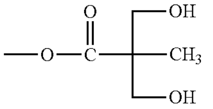 | OH | H | H |
| 22a | $OCH_3$ | $OCH_3$ | 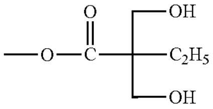 | 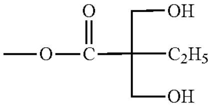 | H | H |
| 22b | $OCH_3$ | $OCH_3$ | 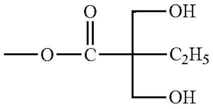 | OH | H | H |
| 23a | H | H | 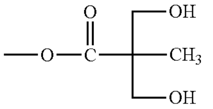 | 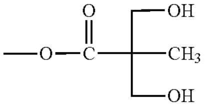 | H | H |
| 23b | H | H | 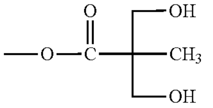 | OH | H | H |
| 24a | 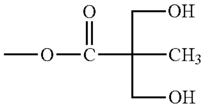 | 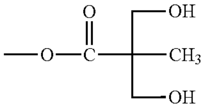 | $OCH_3$ | $OCH_3$ | H | H |
| 24b | 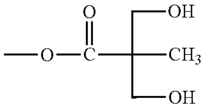 | OH | $OCH_3$ | $OCH_3$ | H | H |
| 25 | 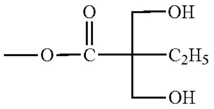 | OH | $OCH_3$ | $OCH_3$ | H | H |
| 26 | $OC_2H_5$ | $OC_2H_5$ | 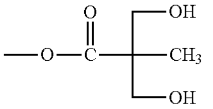 | 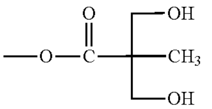 | H | H |
| 27 | $OC_2H_5$ | $OC_2H_5$ | 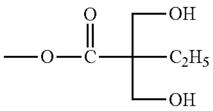 | 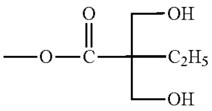 | H | H |

TABLE 1-continued

| Compound | $R_a$ | $R_a'$ | $R_b$ | $R_b'$ | $R_c$ | $R_e$, $R_e'$ |
|---|---|---|---|---|---|---|
| 31 | $C_2H_5$ | $C_2H_5$ | 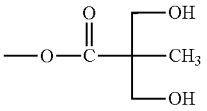 | 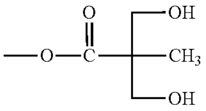 | H | $C_2H_5$ |
| 33 | $OCH_3$ | $OCH_3$ | 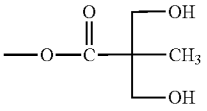 | $OCH_3$ | H | H |
| 35a | $OCH_3$ | $OCH_3$ | 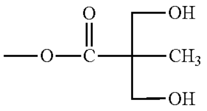 | 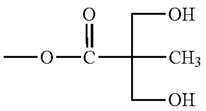 | $CH_3$ | H |
| 35c | $OCH_3$ | $OCH_3$ | 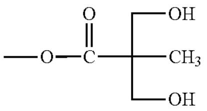 | 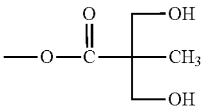 | benzyl | H |
| 35d | $OCH_3$ | $OCH_3$ | 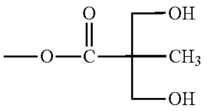 | 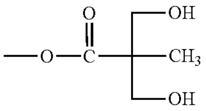 | propargyl | H |
| 35e | $OCH_3$ | $OCH_3$ | 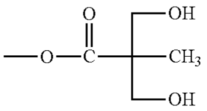 | 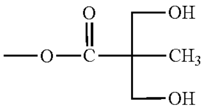 | allyl | H |
| 36 | H | H | 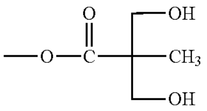 | 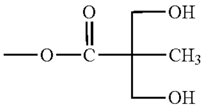 | $CH_3$ | H |
| 37 | 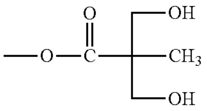 | 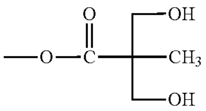 | $OCH_3$ | $OCH_3$ | $CH_3$ | H |

Structures of Compound 21a-((1E,3Z,6E)-3-hydroxy-5-oxohepta-1,3,6-triene-1,7-diyl)bis(2-methoxy-4,1-phenylene)bis(3-hydroxy-2-hydroxymethyl)-2-methylpropanoate, Compound 35a-((1E,6E)-4,4-dimethyl-3,5-dioxohepta-1,6-diene-1,7-diyl)bis(2-methoxy-4,1-phenylene)bis(3-hydroxy-2-hydroxymethyl)-2-methylpropanoate, Compound 35d-((1E,6E)-3,5-dioxo-4,4-di(prop-2-yn-1-yl)hepta-1,6-diene-1,7-diyl)bis(2-methoxy-4,1-phenylene)bis(3-hydroxy-2-(hydroxy methyl)-2-methylpropanoate), Compound 36-((1E,6E)-4,4-dimethyl-3,5-dioxohepta-1,6-diene-1,7-diyl)bis(4,1-phenylene)bis(3-hydroxy-2-(hydroxymethyl)-2-methylpropanoate), and Compound 37-((1E,6E)-4,4-dimethyl-3,5-dioxohepta-1,6-dien-1,7-diyl)bis(2-methoxy-5,1-phenylene)bis(3-hydroxy-2-(hydroxymethyl)-2-methylpropanoate) are shown in Table 2.

TABLE 2

| Compound | Structure |
|---|---|
| 21a | 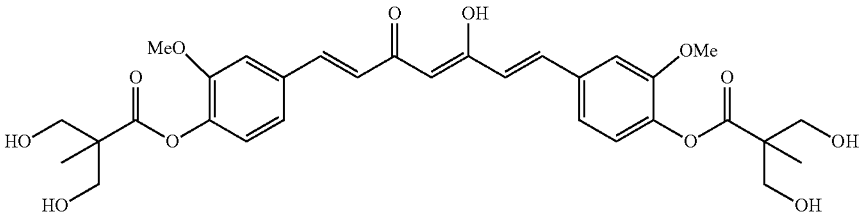 [SMILES: COc1cc(/C=C/C(=O)/C=C(O)/C=C/c2ccc(OC(=O)C(C)(CO)CO)c(OC)c2)ccc1OC(=O)C(C)(CO)CO] |

TABLE 2-continued

| Compound | Structure |
| --- | --- |
| 35a | 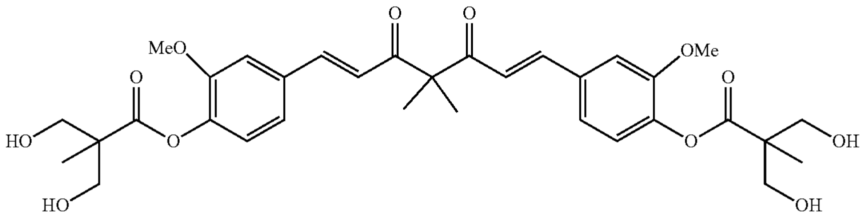 [SMILES: COc1cc(/C=C/C(=O)C(C)(C)C(=O)/C=C/c2ccc(OC(=O)C(C)(CO)CO)c(OC)c2)ccc1OC(=O)C(C)(CO)CO] |
| 35d | 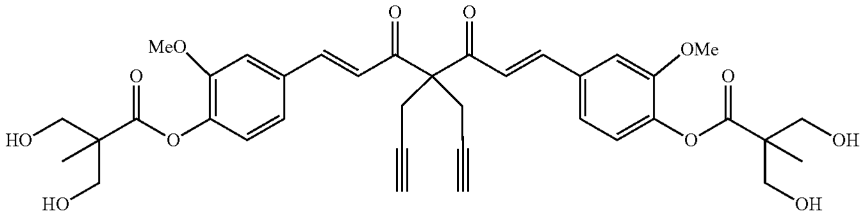 [SMILES: C#CCC(CC#C)(C(=O)/C=C/c1ccc(OC(=O)C(C)(CO)CO)c(OC)c1)C(=O)/C=C/c1ccc(OC(=O)C(C)(CO)CO)c(OC)c1] |
| 36 | 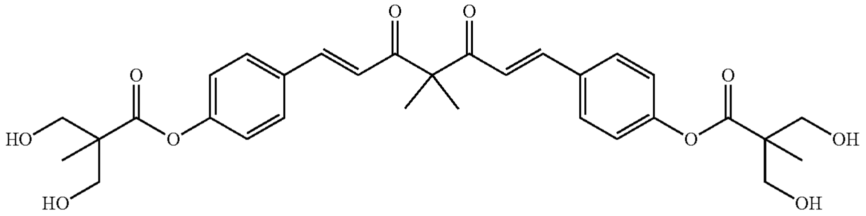 [SMILES: CC(CO)(CO)C(=O)Oc1ccc(/C=C/C(=O)C(C)(C)C(=O)/C=C/c2ccc(OC(=O)C(C)(CO)CO)cc2)cc1] |
| 37 | 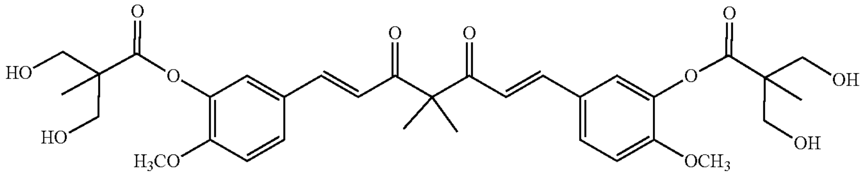 [SMILES: COc1ccc(/C=C/C(=O)C(C)(C)C(=O)/C=C/c2ccc(OC)c(OC(=O)C(C)(CO)CO)c2)cc1OC(=O)C(C)(CO)CO] |

The structure of Compound 21a includes a heptadiene-3,5-dione moiety, which can be readily interconvertible between the keto form and enol form. The 3- or 5-OH group of the enol form combines with the adjacent 5- or 3-C═O through hydrogen bonds to stabilize the structure thereof. In the present disclosure, two methyl functionalities are incorporated onto the 4-position of Compound 21a and afforded ((1E,6E)-4,4-dimethyl-3,5-dioxohepta-1,6-diene-1,7-diyl) bis(2-methoxy-4,1-phenylene)bis(3-hydroxy-2-hydroxymethyl)-2-methyl propanoate (Compound 35a), which is found to possess stable keto form, and is not able to tautomerization. In addition, in the present disclosure, Compound 35a is used as a new lead compound and derived into a series of 4,4-dialkyl derivatives thereof (Compound 35a, Compound 35d, Compound 36 and Compound 37) with stable keto form.

2. Inhibitory Growth Effect of the Diarylheptanoid Compound of the Present Disclosure on the EGFR Gene Mutant NSCLC Cells and the EGFR-TKIs Resistant is NSCLC Cells The EGFR gene mutant NSCLC cells were treated with the diarylheptanoid compounds of the present disclosure, and then the cell survival was stained with crystal violet to measure the $IC_{50}$ values of the diarylheptanoid compounds of the present disclosure in the EGFR gene mutant NSCLC cells, so as to determine the growth inhibitory effect of the diarylheptanoid compounds of the present disclosure on the EGFR gene mutant NSCLC cells.

EGFR gene mutations in lung cancer are mostly found in exons 18-21, which are the intracellular tyrosine kinase coding region. The most common mutations include E746-A750del in exon 19 and L858R point mutation in exon 21, which account for about 85%-90% of EGFR gene mutations. Tumor cells with these two mutations are sensitive to the EGFR-TKIs, known as activating mutations. Secondary mutations may occur in some tumor cells, and the most common secondary mutation is the T790M mutation in exon 20, which is a drug resistance mutation. Please refer to FIG. 1A, which shows the analysis result of the inhibition of the H1650 cells growth by the diarylheptanoid compounds of the present disclosure. The H1650 cells have the E746-A750del mutation in exon 19 of the EGFR gene, wherein the CCM represents curcumin and the BDMC represents bisdemethoxycurcumin. The $IC_{50}$ value of the compound>16 μM shows that the H1650 cells have not yet reached 50% cell growth inhibition after treatment with compounds at concentrations as high as 16 μM, and data in FIG. 1A are represented by mean±SD (n=3).

FIG. 1A shows the $IC_{50}$ values in the H1650 cells treated with 22 diarylheptanoid compounds (including BDMC) and curcumin for 3 days. 18 is diarylheptanoid compounds including Compound 1, Compound 24b, Compound 23b, Compound 33, Compound 25, Compound 35b, Compound 22a, Compound 21a, Compound 22b, Compound 26, Compound 36, Compound 35a, Compound 35c, Compound 27, Compound 31, Compound 37, Compound 35e and Compound 35d have significantly better inhibitory activity than the parent compound—curcumin on the growth of the H1650 cells, wherein  represents $p<0.05$, * represents $p<0.01$, **** represents $p<0.001$.

Experimentally, another 7 EGFR-TKIs resistant NSCLC cells were treated with Compound 21a, Compound 35a, Compound 35d, Compound 36 or Compound 37, and then the cell survival assay was performed to measure the $IC_{50}$ values of the diarylheptanoid compounds of the present disclosure in the EGFR-TKIs resistant NSCLC cells, so as to determine the growth inhibitory effect of the diarylheptanoid compounds of the present disclosure on the EGFR-TKIs resistant NSCLC cells. The EGFR-TKIs resistant NSCLC cells used in the test include the H1975 cells, the GR2 cells, the GR5 cells, the GR6 cells, the GR8 cells, the GR9 cells and the GR10 cells, in which the H1975 cells have a point mutation of L858R in exon 21 and a secondary mutation of T790M in exon 20; the GR2 cells, the GR5 cells, the GR6 cells, the GR8 cells, the GR9 cells and the GR10 cells are gefitinib-resistant cell lines obtained after treating gefitinib with the HCC827 cells as parental cells, while the HCC827 cells and the H1650 cells are the NSCLC cells with E746-A750del mutation of EGFR exon 19.

Figure 1B:
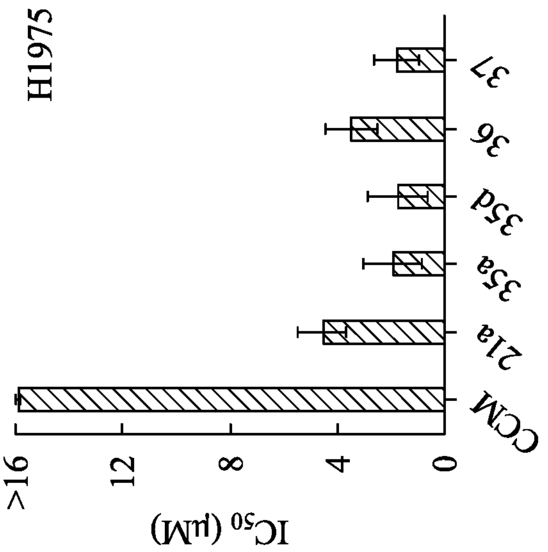
FIG. 1B, FIG. 1C and FIG. 1D show the analysis results of the inhibition of the growth of the epidermal growth factor receptor-tyrosine kinase inhibitors resistant non-small cell lung cancer (NSCLC) cells by the diarylheptanoid compounds of the present disclosure.
Figure 1C:
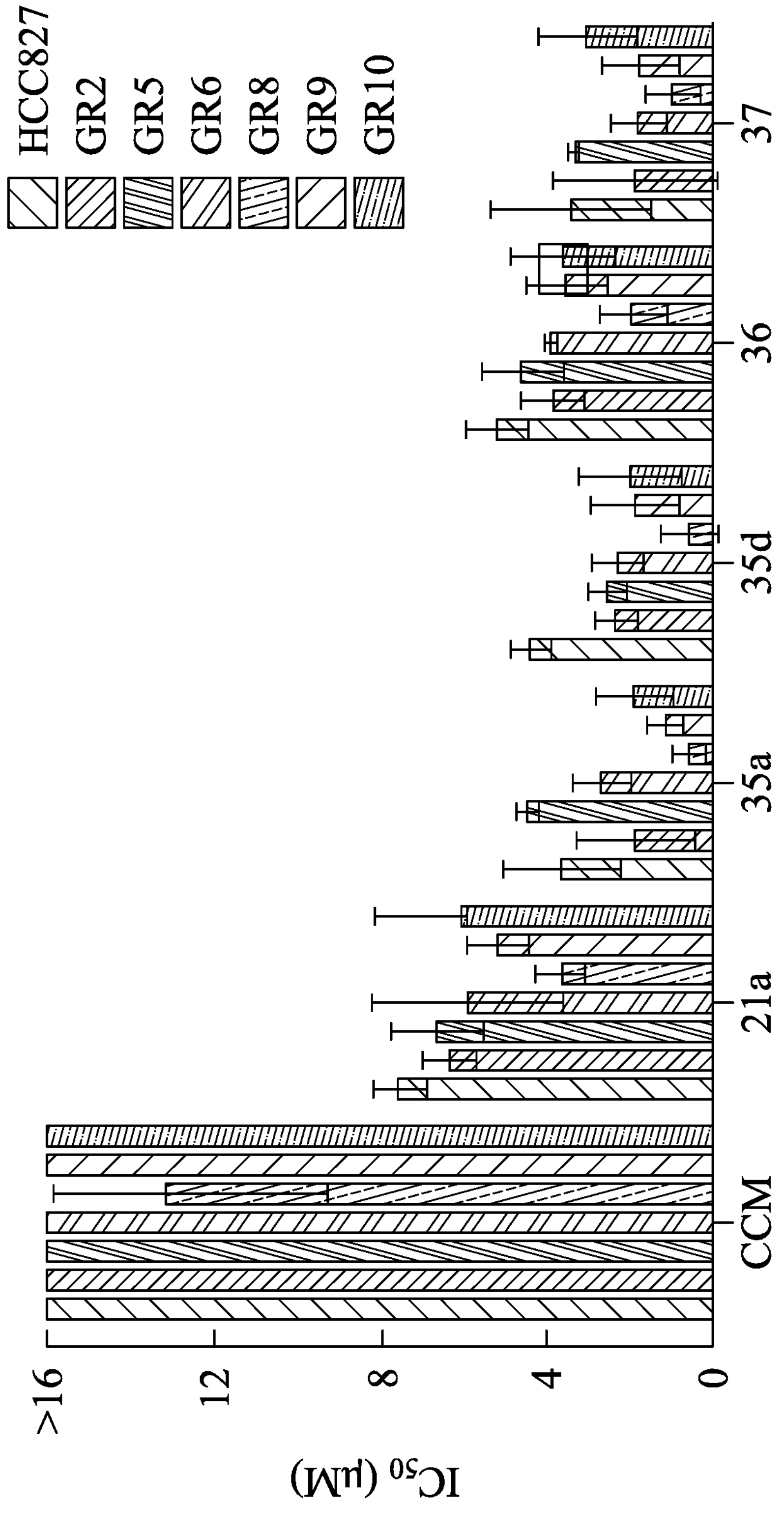
Figure 1D:
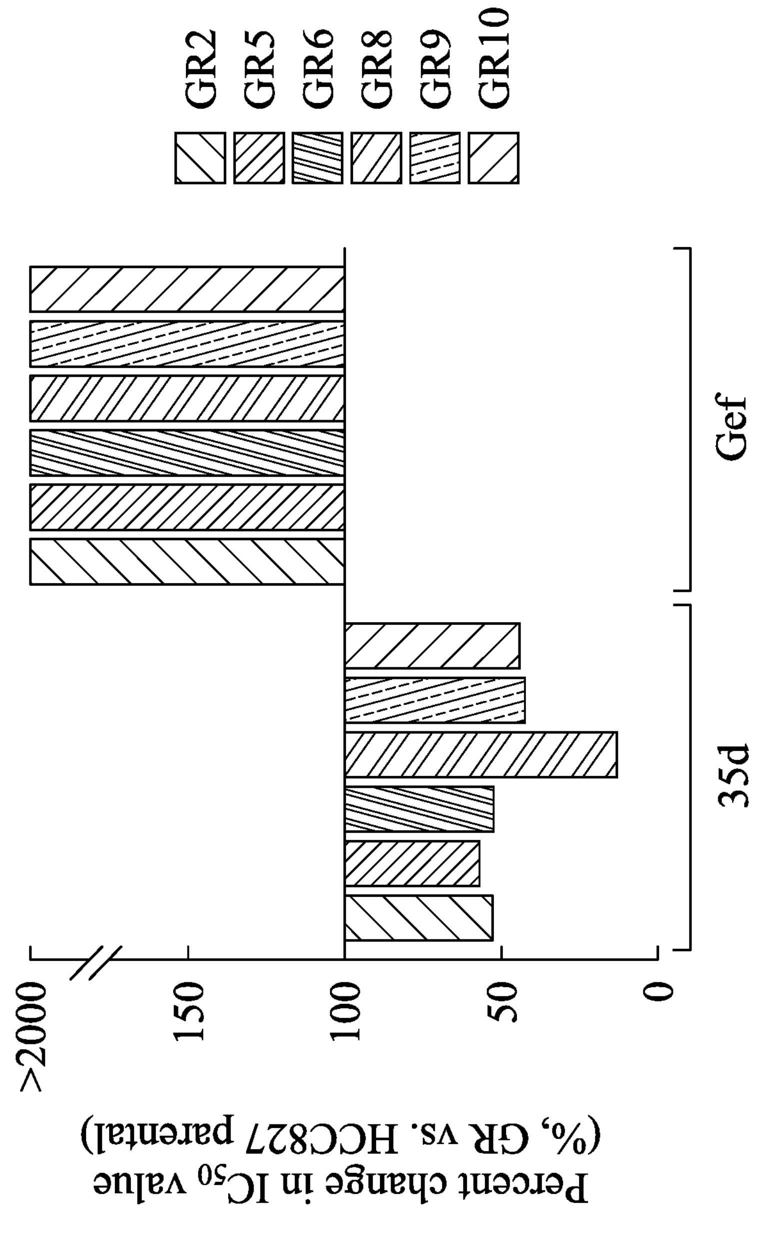

Please refer to FIG. 1B, FIG. 1C and FIG. 1D. FIG. 1B shows the analysis result of the inhibition of the H1975 cells growth by the diarylheptanoid compounds of the present disclosure. FIG. 1C shows the analysis result of the is inhibition of the GR2 cells, the GR5 cells, the GR6 cells, the GR8 cells, the GR9 cells and the GR10 cells growth by the diarylheptanoid compounds of the present disclosure. FIG. 1D shows the percentage changes of the $IC_{50}$ values after the GR2 cells, the GR5 cells, the GR6 cells, the GR8 cells, the GR9 cells and the GR10 cells were treated with Compound 35d and gefitinib respectively. Data in FIG. 1B and FIG. 1C are presented as mean±SD (n=3), while the $IC_{50}$ value>16 μM show that the test cells have not yet reached 50% cell growth inhibition after treatment with compounds at concentrations as high as 16 μM. Gef in FIG. 1D represents gefitinib.

FIG. 1B shows the measured the $IC_{50}$ values of the H1975 cells treated with Compound 21a, Compound 35a, Compound 35d, Compound 36, Compound 37 and curcumin for 3 days, respectively. The results showed that Compound 21a, Compound 35a, Compound 35d, Compound 36 and Compound 37 of the present disclosure had significantly better inhibitory activity than curcumin on the growth of the H1975 cells.

FIG. 1C shows the measured the $IC_{50}$ values of the GR2 cells, the GR5 cells, the GR6 cells, the GR8 cells, the GR9 cells and the GR10 cells after treatment with Compound 21a, Compound 35a, Compound 35d, Compound 36, Compound 37 and curcumin for 3 days, respectively. The results show that Compound 21a, Compound 35a, Compound 35d, Compound 36 and Compound 37 of the present disclosure have significantly better inhibitory activity than curcumin on the growth of the GR2 cells, the GR5 cells, the GR6 cells, the GR8 cells, the GR9 cells and the GR10 cells.

The results in FIG. 1B and FIG. 1C show that all EGFR-TKIs resistant is NSCLC cells are more sensitive to Compound 21a, Compound 35a, Compound 35d, Compound 36 and Compound 37 than curcumin, and can achieve 50% inhibition of cell growth at significantly lower concentrations.

FIG. 1D shows that the analysis results obtained by comparing the $IC_{50}$ values measured by the GR2 cells, the GR5 cells, the GR6 cells, the GR8 cells, the GR9 cells and the GR10 cells with the $IC_{50}$ value measured by the HCC827 cells, in which the HCC827 cells, the GR2 cells, the GR5 cells, the GR6 cells, the GR8 cells, the GR9 cells and the GR10 cells were treated with Compound 35d and gefitinib for 3 days and then measured the $IC_{50}$ values. The results in FIG. 1D show that all gefitinib-resistant cell lines are indirectly sensitive to Compound 35d. All gefitinib-resistant cell lines were >200-fold more resistant to gefitinib (Gef) than their parental cells, the HCC827 cells.

3. Anticancer Activity of Compound 35d Against the GR6 Tumor, the GR8 Tumor and the HCC827 Tumor In order to verify the anticancer effect of the diarylheptanoid compound of the present disclosure in vivo, the GR6 tumor mouse model, the GR8 tumor mouse model and the HCC827 tumor mouse model of xenotransplantation were first established, and the GR6 tumor mice, the GR8 tumor mice, and the HCC827 tumor mice were treated with 100 mg/kg of Compound 35d daily for 35 days, and the tumor size and body weight of the GR6 tumor mice, the GR8 tumor mice, and the HCC827 tumor mice were recorded.

Figure 2A:
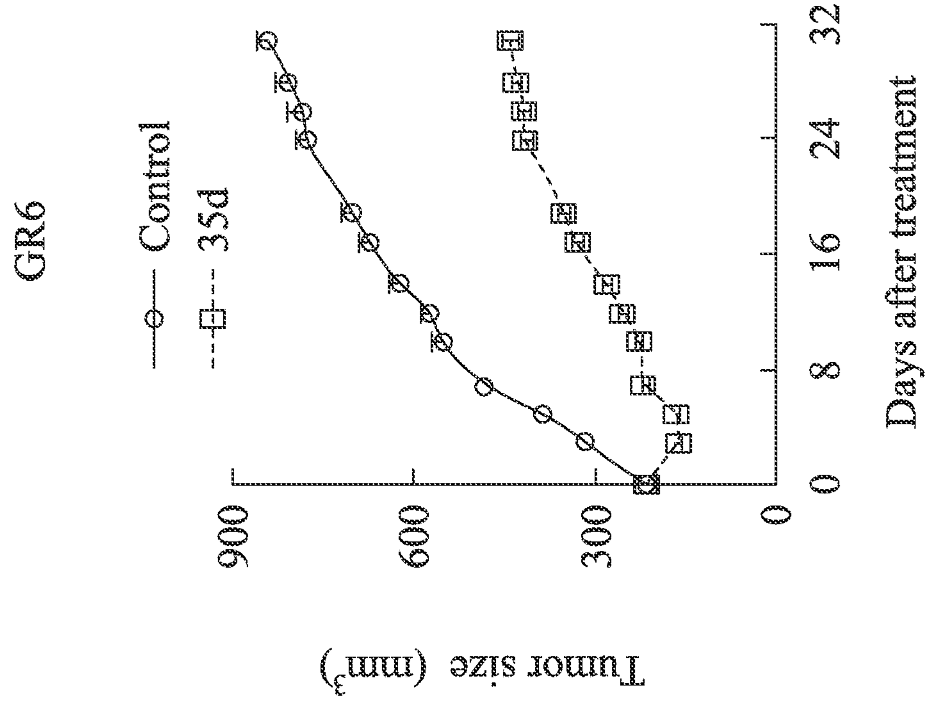
FIG. 2A shows the analysis result of the inhibition of tumor growth in the GR6 tumor mice by treating Compound 35d alone.
Figure 2B:
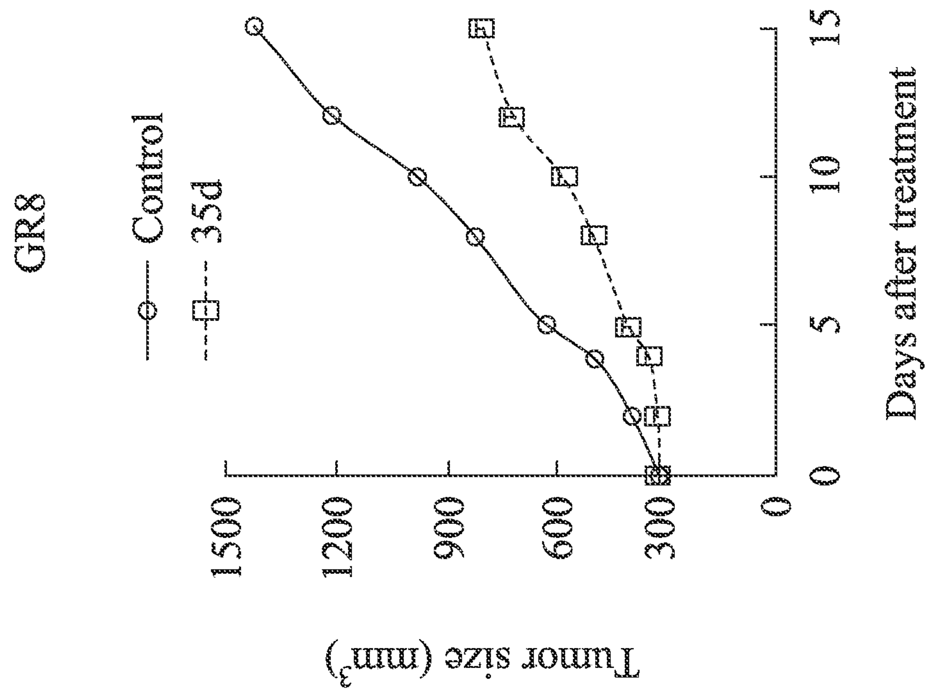
FIG. 2B shows the analysis result of the inhibition of tumor growth in the GR8 tumor mice by treating Compound 35d alone.
Figure 2D:
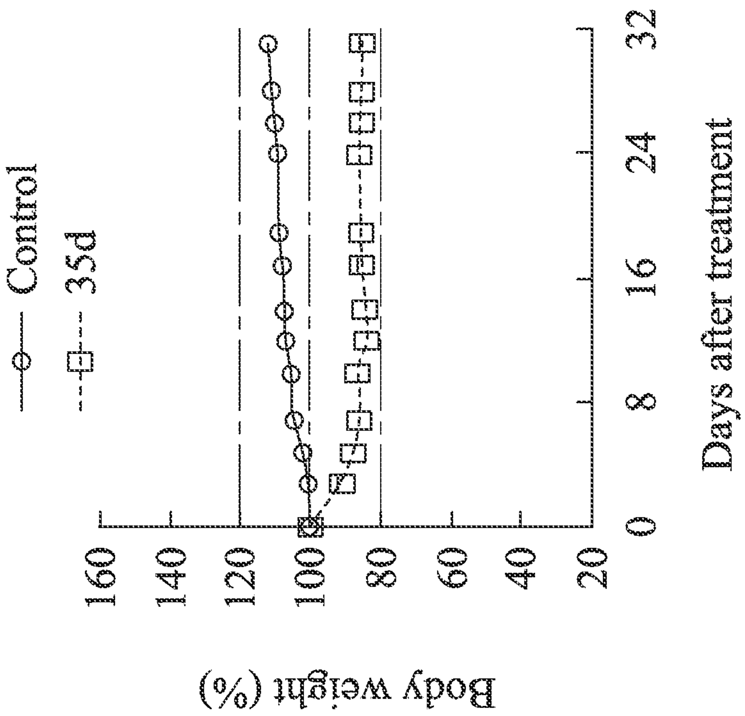
FIG. 2D shows the statistical chart of body weight changes in the tumor mice by treating Compound 35d alone.
Figure 2C:
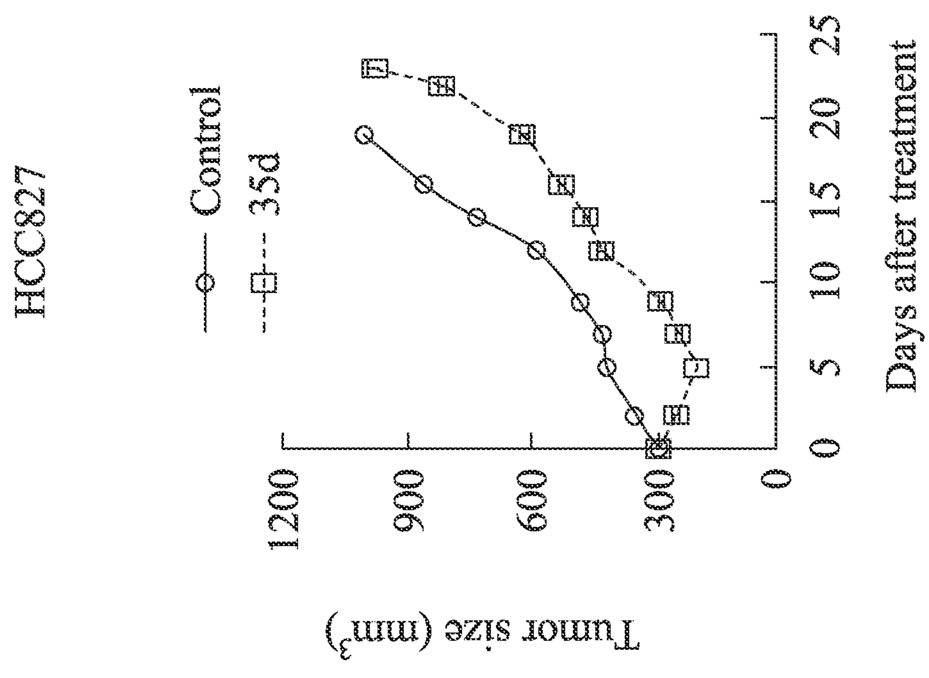
FIG. 2C shows the analysis result of the inhibition of tumor growth in the HCC827 tumor mice by treating Compound 35d alone.

Please refer to FIG. 2A to FIG. 2D, FIG. 2A shows the analysis result of the inhibition of tumor growth in the GR6 tumor mice by treating Compound 35d alone, FIG. 2B shows the analysis result of the inhibition of tumor growth in the GR8 tumor mice by treating Compound 35d alone, FIG. 2C shows the analysis result of the inhibition of tumor growth in the HCC827 tumor mice by treating Compound 35d alone, and FIG. 2D shows the statistical chart of body weight changes in the tumor mice by treating Compound 35d alone, wherein data in FIG. 2A to FIG. 2C are presented as mean t SEM (n=10).

The results in FIG. 2A to FIG. 2C show that Compound 35d significantly inhibits the tumor growth of the GR6 tumor mice and the GR8 tumor mice, but has less significant effect on inhibiting the tumor growth of the HCC827 tumor mice. However, the results in FIG. 2D show that the body weight of the tumor mice did not decrease significantly after being treated with Compound 35d for more than 1 month.

4. Combined Treatment of Compound 35d and Osimertinib Inhibits the Re-Progression of the GR6 Tumor EGFR-TKIs are currently the standard treatment for NSCLC patients with the EGFR gene mutation. To further test whether the combined use of the diarylheptanoid compound of the present disclosure and known drug can enhance the therapeutic effect of NSCLC, the GR6 tumor mice were divided into 4 groups. One group received 100 mg/kg Compound 35d treatment per day (represented as 35d), another group received 1 mg/kg osimertinib treatment per day (represented as Osi), still another group received the combined treatment of 100 mg/kg Compound 35d and 1 mg/kg osimertinib per day (represented as 35d+Osi), and the other group was the control group without drug treatment.

Figure 3B:
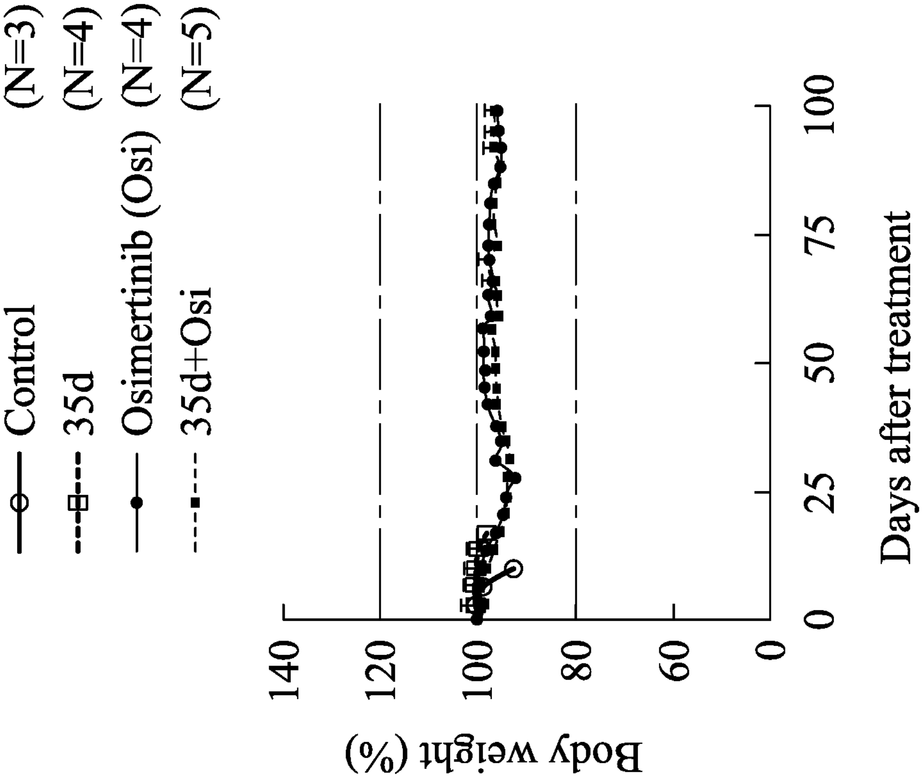
FIG. 3B shows the statistical chart of body weight changes in the GR6 tumor mice by treating the combined treatment of Compound 35d and osimertinib.
Figure 3A:
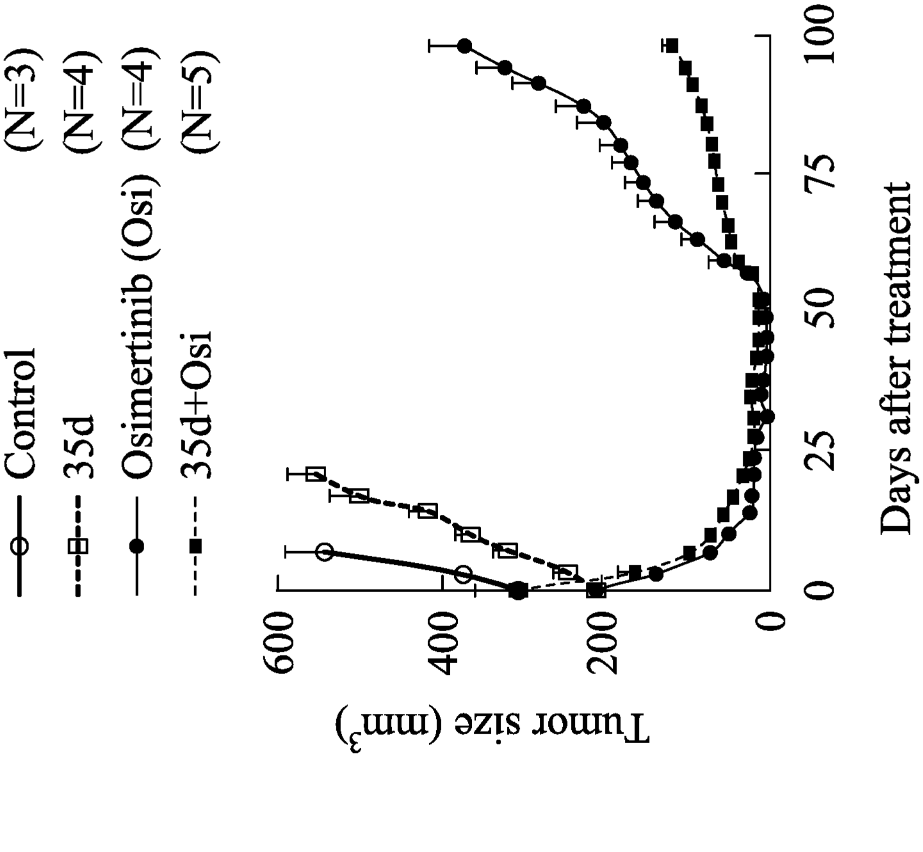
FIG. 3A shows the analysis result of the inhibition of tumor re-progression in the GR6 tumor mice by treating a combined treatment of Compound 35d and osimertinib.

Please refer to FIG. 3A and FIG. 3B, FIG. 3A shows the analysis result of the inhibition of tumor re-progression in the GR6 tumor mice by treating the combined treatment of Compound 35d and osimertinib, and FIG. 3B shows the statistical chart of body weight changes in the GR6 tumor mice by treating the combined treatment of Compound 35d and osimertinib, wherein data in FIG. 3A and FIG. 3B are represented by mean±SEM (n=10).

The results in FIG. 3A show that although the tumor size of the GR6 tumor mice in the Osi group was initially reduced by osimertinib treatment, the treated tumors subsequently re-growth, indicating that the tumors of the GR6 tumor mice have EGFR-TKIs resistance. However, no matter in the group treated with Compound 35d alone or in the group treated with the combined treatment of Compound 35d and osimertinib, tumor re-progression in the GR6 tumor mice was significantly inhibited. And the results in FIG. 3B show that neither the single treatment of Compound 35d nor the combined treatment of Compound 35d and osimertinib can significantly reduce the body weight of mice.

To sum up, the present disclosure provides a new use of the pharmaceutical composition, which can be used to manufacture a drug for treating lung cancer. The pharmaceutical composition includes the diarylheptanoid compound or the pharmaceutically acceptable salt thereof, which can inhibit the growth of the EGFR gene mutant NSCLC cells and the EGFR-TKIs resistant NSCLC cells, so that can be used to manufacture the drug for treating lung cancer. Moreover, the pharmaceutical composition can have a synergistic effect when used in combination with EGFR-TKIs, which can increase the effectiveness of treating lung cancer, especially for the treatment of lung cancer with the EGFR gene mutation and EGFR-TKIs resistant, and has the potential to be used in the medical and health care market.

Although the present disclosure has been described as above by way of embodiments, it is not intended to limit the present disclosure. Person having skilled in the art can make various changes and modifications without departing from the spirit and scope of the present disclosure. Therefore, the scope of protection of the present disclosure should be defined by the scope of the appended patent application.

What is claimed is:

1. A method for treating a lung cancer comprising administering a pharmaceutical composition comprising a diarylheptanoid compound or a pharmaceutically acceptable salt thereof, wherein the diarylheptanoid compound is selected from the group consisting of:

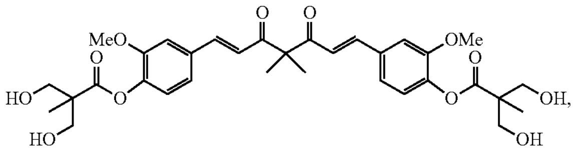

-continued

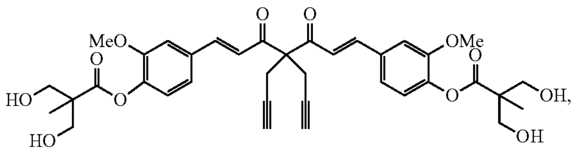

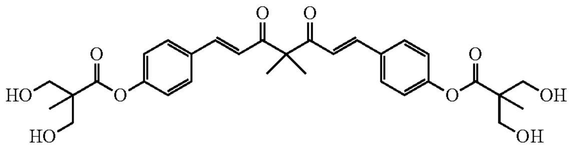

and

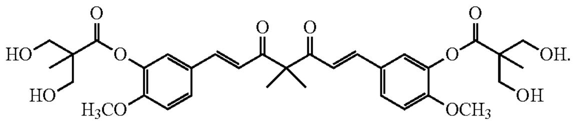

2. The method for treating the lung cancer of claim 1, wherein the pharmaceutical composition further comprises epidermal growth factor receptor-tyrosine kinase inhibitors (EGFR-TKIs).

3. The method for treating the lung cancer of claim 2, wherein the EGFR-TKIs are osimertinib, gefitinib, erlotinib or afatinib.

4. The method for treating the lung cancer of claim 1, wherein the lung cancer is a non-small cell lung cancer.

5. The method for treating the lung cancer of claim 1, wherein the lung cancer is resistant to epidermal growth factor receptor-tyrosine kinase inhibitors.

* * * * *